United States Patent [19]
Dardel

[11] Patent Number: 5,341,810
[45] Date of Patent: Aug. 30, 1994

[54] STERILE PUNCTURING DEVICE FOR BLOOD VESSELS WITH A NON-STERILE ULTRASOUND PROBE, AND APPARATUS FOR PREPARING THE DEVICE

[75] Inventor: Eric Dardel, Seuzach, Switzerland

[73] Assignee: Sulzer Medizinaltechnik AG, Winterthur, Switzerland

[21] Appl. No.: 967,368

[22] Filed: Oct. 28, 1992

[30] Foreign Application Priority Data

Oct. 29, 1991 [CH] Switzerland ............ 03157/91

[51] Int. Cl.$^5$ ............................................. A61B 8/00
[52] U.S. Cl. ............................................. 128/662.05
[58] Field of Search ............ 128/660.03, 662.05, 128/662.06

[56] References Cited

U.S. PATENT DOCUMENTS

| | | | |
|---|---|---|---|
| 3,556,079 | 1/1971 | Omizo | 128/662.05 |
| 4,108,165 | 8/1978 | Kopp | 128/662.05 |
| 4,898,178 | 2/1990 | Wedel | 128/662.05 |
| 5,052,396 | 10/1991 | Wedel et al. | 128/662.05 |
| 5,076,279 | 12/1991 | Arenson et al. | 128/662.05 |

FOREIGN PATENT DOCUMENTS 3329041  2/1984  Fed. Rep. of Germany .
WO/84/030-34  8/1984  PCT Int'l Appl. .

Primary Examiner—Francis Jaworski
Attorney, Agent, or Firm—Townsend and Townsend Khourie and Crew

[57] ABSTRACT

A sterile puncturing device for blood vessels is disclosed which has an ultrasound probe (1) capable of non-sterile use. The probe (1) can be introduced into a capsule (12, 13) in the puncturing device. The apparatus has a fluid-tight bag (16) with sterile contents (10), the bag containing a holder (11) with the capsule for the ultrasound probe, and an entrance lock in the bag wall communicates with the opened capsule. The apparatus is disposable. The ultrasound probe, which can be used repeatedly, is introduced into the device shortly before puncturing.

15 Claims, 4 Drawing Sheets

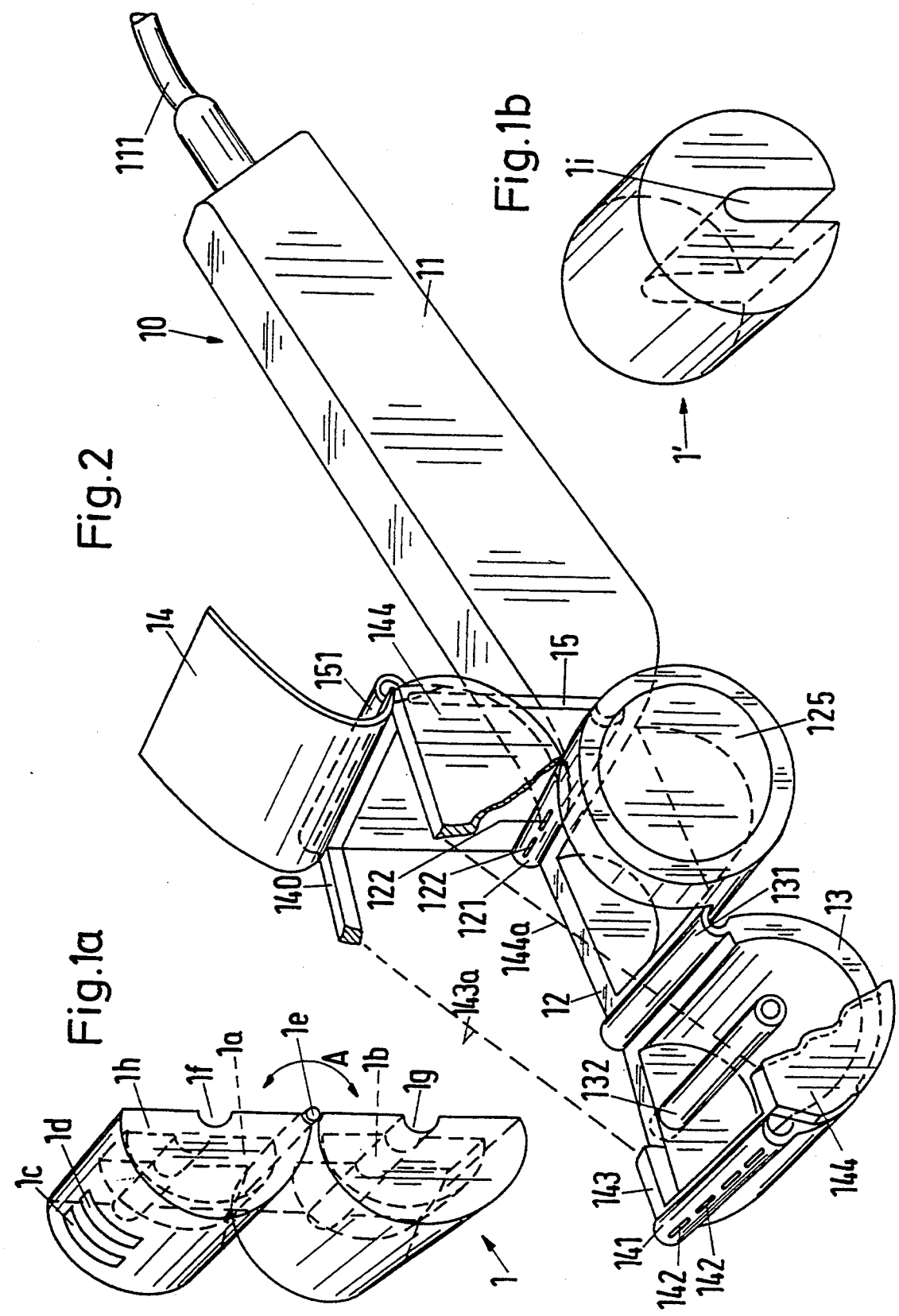

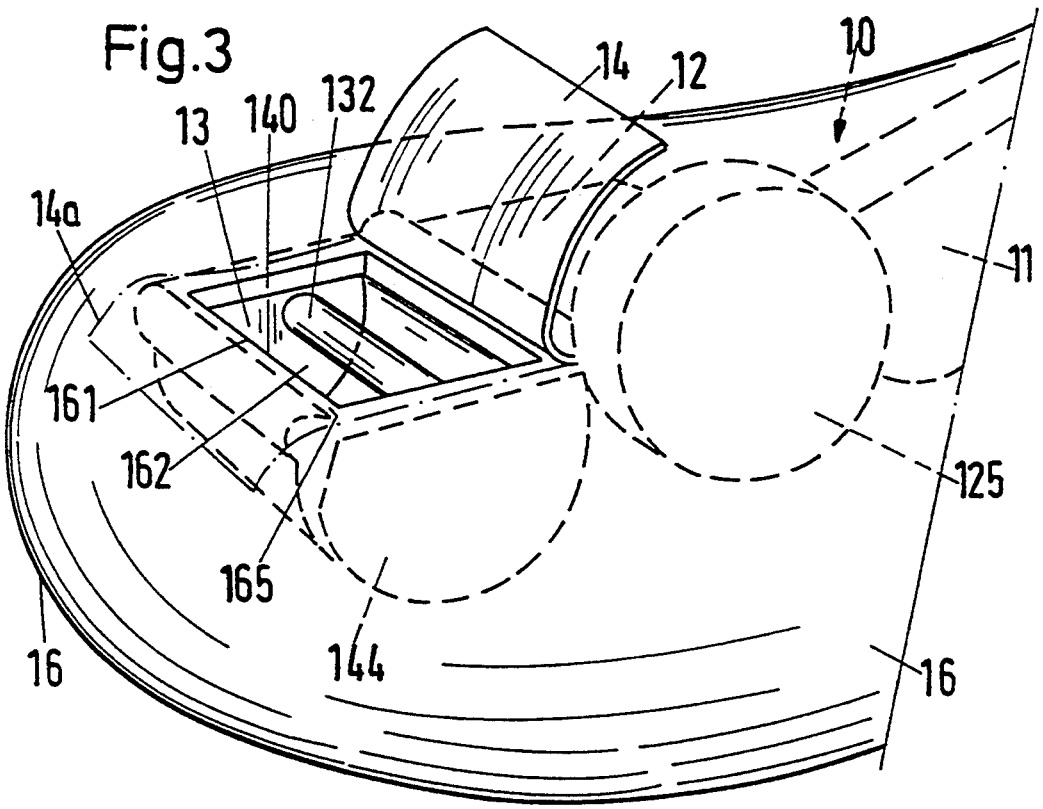
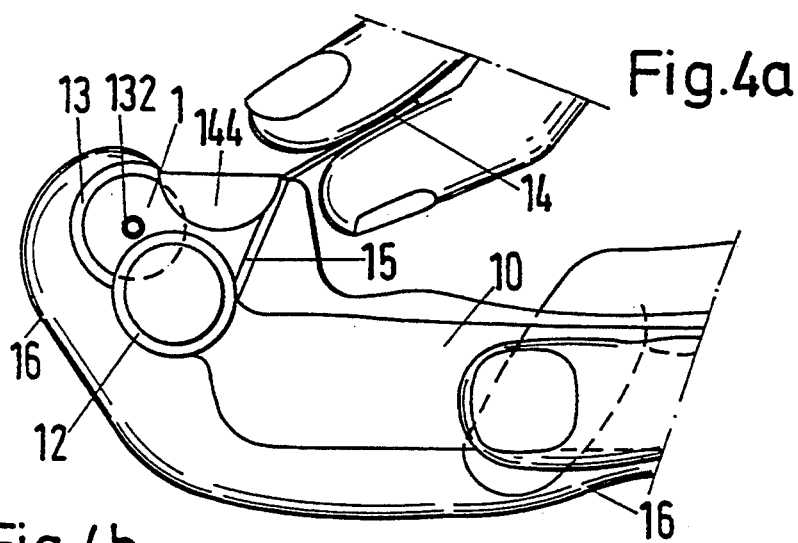
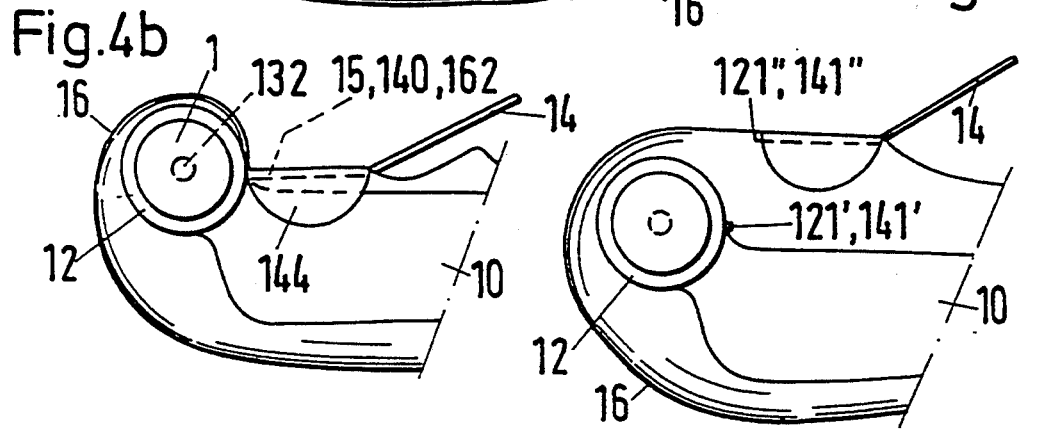

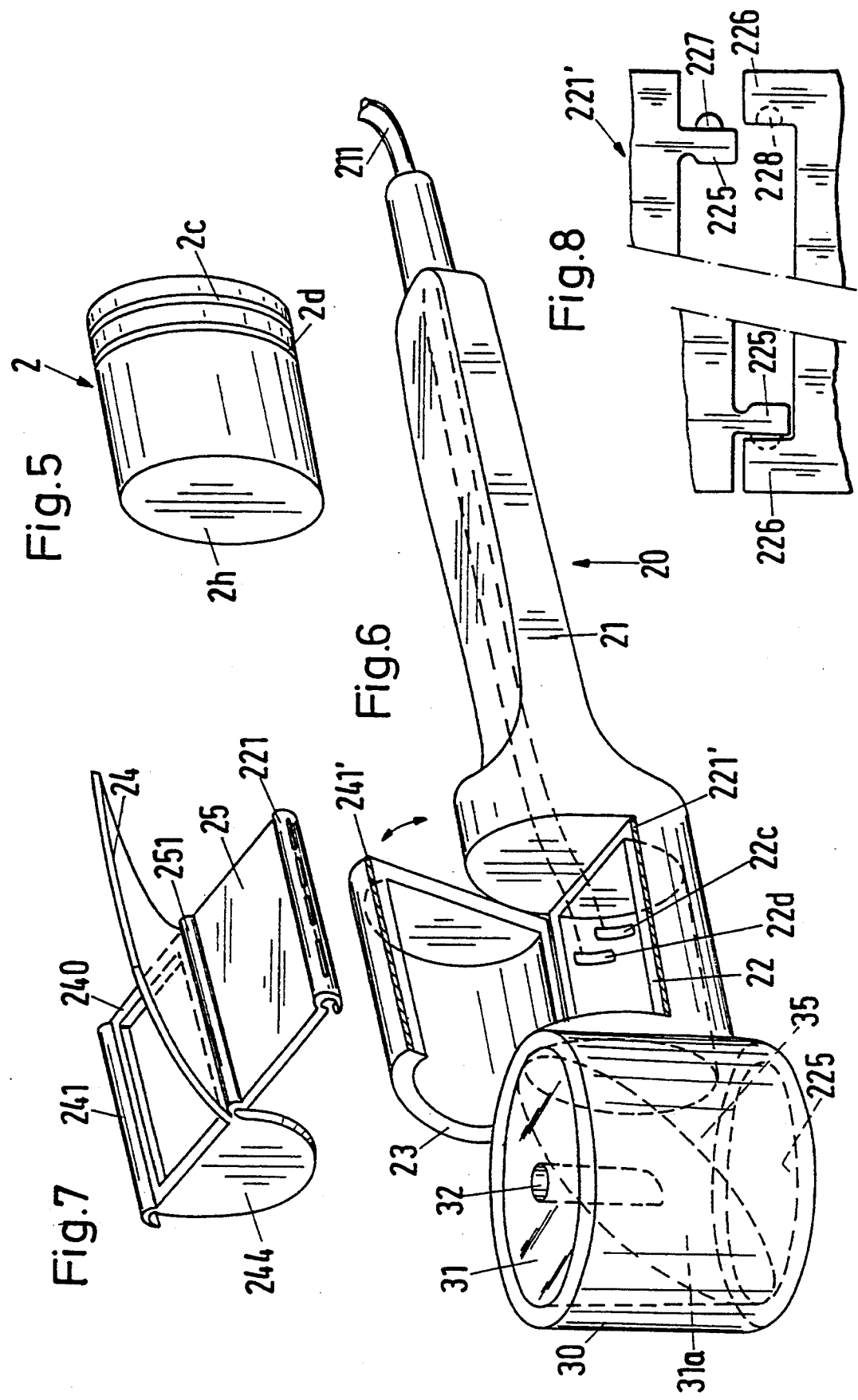

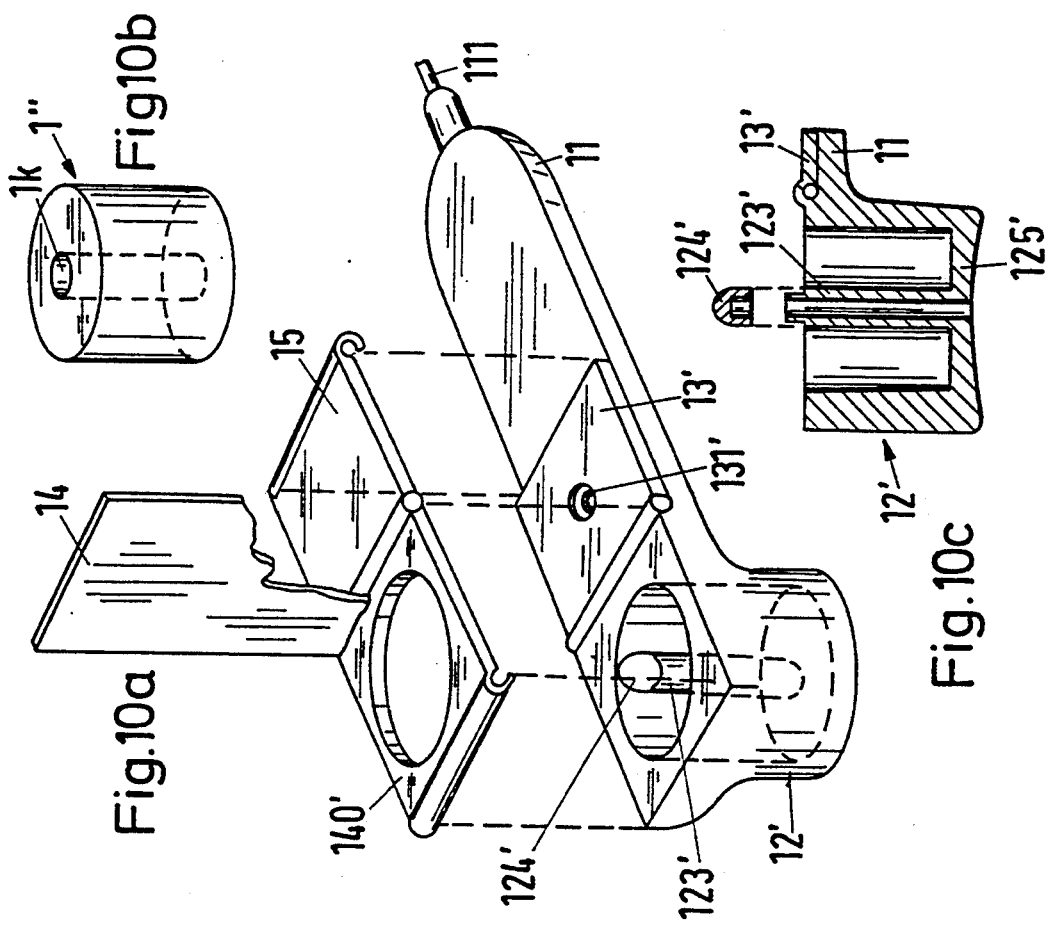
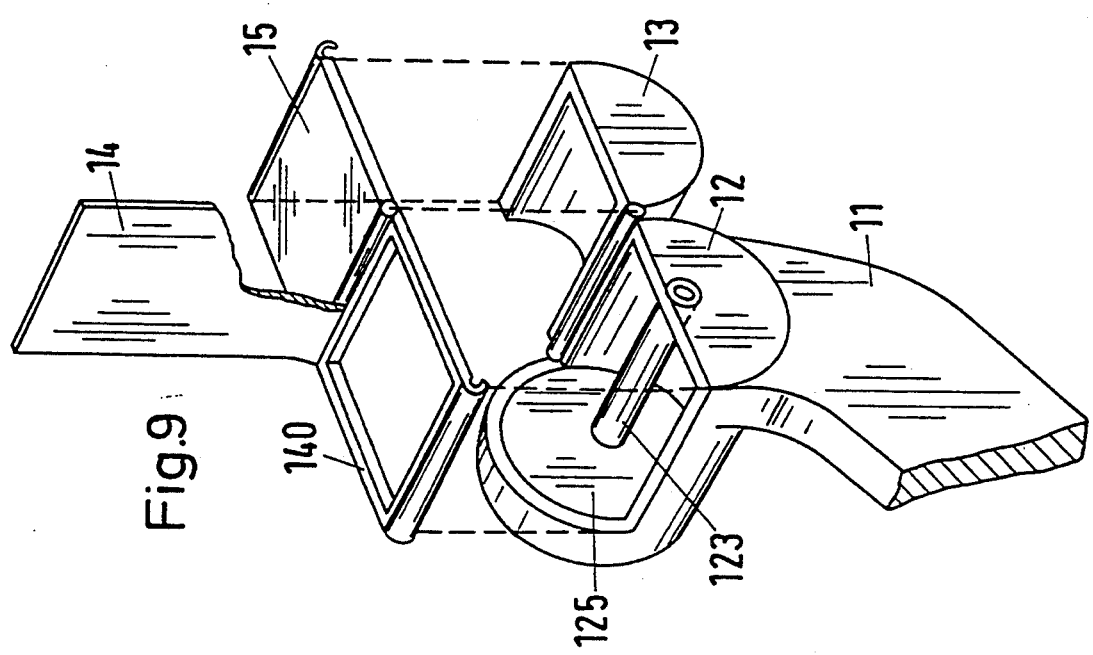

STERILE PUNCTURING DEVICE FOR BLOOD VESSELS WITH A NON-STERILE ULTRASOUND PROBE, AND APPARATUS FOR PREPARING THE DEVICE

BACKGROUND OF THE INVENTION

The invention relates to apparatus for preparing a sterile puncturing device for blood vessels in which a non-sterile ultrasound probe can be used, and to a puncturing device of this type.

The ultrasound probe in such a device has a transmitter/receiver system by means of which ultrasound can be irradiated into the body and a signal from the partly reflected beam can be recorded. Due to the Doppler effect, reflection by the flowing blood leads to a frequency shift from which an acoustic and/or optical signal can be obtained. By seeking a maximum for such a signal it is possible to find the point of penetration for the puncturing needle.

Devices of this type are known, for example, from Swiss Patent Specification No. 676 787. The transmitter/receiver system disclosed therein is so constructed that a guide duct for the needle runs through the acoustic resonator. This design is disadvantageous because puncturing must be performed under sterile conditions and because the required gas sterilization of the ultrasound probe is very time-consuming. In a simpler ultrasound probe without an integrated guide duct sterility can be achieved with a sterile covering intended for use once only (see for example EP-A 0 104 618). In these simpler probes, however, the needle cannot run coaxial with the ultrasound beam transmitted.

SUMMARY OF THE INVENTION

The problem underlying the invention is to create on the one hand, a puncturing device with which a non-sterile ultrasound probe can be used, and, on the other hand, apparatus by means of which the puncturing device can be prepared for use under sterile conditions. In addition, the puncturing device of the present invention at least approximately guides the coaxial needle in the direction of the transmitted beam.

The puncturing device in accordance with the invention comprises, in addition to a capsule and a holder, a stationary device portion with, for example, optical and/or acoustic indicator means and a connecting cable for the power supply to the ultrasound probe and for signal transmission. The stationary device portion need not be sterile if it is far enough from the treatment area; alternatively, it may be enclosed in a sterile sack. The connecting cable, which can be plugged into the stationary device, portion must be sterile; it is part of the contents of the bag in the apparatus according to the invention. The non-sterile ultrasound probe is introduced shortly before puncturing. Afterwards the bag is opened (for example, torn open) and the contents are passed to the physician in a sterile manner.

Various embodiments of the puncturing device according to the invention are described by way of examples. In one a cylindrical ultrasound probe is used. On the capsule there is a coupling member for the ultrasound beam generated in the probe and reflected in the body. In this coupling member there are a reflector for deflecting the ultrasound and a guide for a puncturing needle. The guide is designed so that the puncturing needle can be moved at least approximately coaxially with the direction of the transmitted beam.

In a second embodiment the ultrasound probe comprises two cylinder halves connected by a hinge. One half contains the transmitter and the other the receiver of the ultrasound probe (cf. e.g. U.S. Pat. No. 3,556,079). In the capsule there is a tubular guide for the puncturing needle, which runs along the longitudinal axis of the closed probe inserted, and which as well as guiding shields the puncturing needle relative to the non-sterile probe. The probe may alternatively comprise a cylinder with a groove, in which case the needle guide can be pushed into the groove.

In another embodiment the cylindrical probe has an axial, laterally closed duct instead of the groove. As regards ultrasound location, it should be noted that it is of course possible to provide a single pulsed oscillatory crystal which acts both as transmitter and receiver for the ultrasound probe.

The apparatus in accordance with the invention and the associated probe portion, comprising a capsule, holder and connecting cable but excluding the ultrasound probe, are designed to be disposable. The manufacturing material is preferably synthetic plastics, although individual components, for example the ultrasound reflector, may be made from metal or other materials.

BRIEF DESCRIPTION OF THE DRAWINGS

FIG. 1a illustrates an ultrasound probe comprising two cylinder halves connected by a hinge;

FIG. 1b shows an ultrasound probe in the form of a cylinder with a groove;

FIG. 2 shows the probe portion of a puncturing device made in accordance with the invention for the ultrasound probe shown in FIGS. 1a or 1b;

FIG. 3 illustrates part of the apparatus made in accordance with the invention for preparing the puncturing device shown in FIG. 2;

FIGS. 4a to c illustrate three phases during the introduction of the ultrasound probe by means of the apparatus shown in FIG. 3;

FIG. 5 shows a cylindrical ultrasound probe;

FIG. 6 shows a probe portion for the ultrasound probe shown in FIG. 5;

FIG. 7 illustrates parts of the entrance lock of the apparatus in accordance with the invention;

FIG. 8 shows a hinge with snap-fastening-type joints;

FIG. 9 shows a variant of the apparatus shown in FIG. 3; and

FIGS. 10a to c show another variant embodiment.

DESCRIPTION OF THE PREFERRED EMBODIMENTS

The ultrasound probe 1 illustrated in FIG. 1a comprises a transmitter 1a and a receiver 1b which are connected to two contacts 1c, 1d on the surface of the probe. The two halves of the probe 1 can be closed by folding them about the hinge 1e to form a circular cylinder as indicated by a double arrow A. In the closed condition the probe 1 has a needle guiding duct formed by the two parts 1f, 1g. The ultrasound beam generated in the transmitter 1a is transmitted through the end face 1h. FIG. 1b illustrates an alternative ultrasound probe 1' with a groove 1i by means of which the probe 1' can be pushed over the needle guide. The contacts (not shown) corresponding to the contacts 1c, 1d may be provided on the inside lateral surfaces of the groove 1i.

The probe portion 10 in FIG. 2 comprises the holder 11, which acts as a handle, the connecting cable 111, of which only a short length is shown, and the capsule comprising the two shell portions 12, 13 for the ultrasound probe 1 or 1'. The two shell portions 12, 13 are connected together by a hinge 131. By means of two further hinges 121, 141 the capsule is connected to components of the apparatus in accordance with the invention (not shown in its entirety), these components being parts of the entrance lock. FIG. 3 shows how the probe portion 10 is mounted in the bag 16 of the apparatus according to the invention.

The components of the entrance lock are the first lid 14 on the frame 140 and the second lid 15, which is connected to the frame 140 by a hinge 151. The frame reinforces the edge 161 of the bag opening 162. The first lid 14 is secured to the frame 140 along the hinge 151; before introduction of the probe it closes the bag opening 162 in a fluid-tight manner, but is releasably connected to the edge 161. (Chain lines in FIG. 3 show the lid edge 14a with the bag 26 sealed.) The frame is formed perpendicularly to the two hinges 141, 151 by the cross member 143 and the upper edge of the shield 144. (These two components 143, 144 are both shown broken in two in FIG. 2, for representational reasons, and they should be regarded as being joined along the broken lines 143a, 144a.) The hinges 121, 131, 141 and 151 are, for example, film hinges as indicated in FIG. 2.

In FIGS. 2 and 3 the first lid 14 is pulled off the bag opening 162; the ultrasound probe 1 can be placed in the shell portion 13. The shield 144 covers the open-ended cell portion 13 and so prevents direct entry to the sterile interior of the bag when the bag 16 is open. After insertion the ultrasound probe 1 in the closed state embraces the needle guide 132. By pulling the lever 14 as indicated in FIG. 4a it is possible to pivot the shell portion 13 with the inserted probe 1 onto the other shell portion 14 of the capsule, at the same time entraining the second lid 15 and the other parts of the entrance lock. In FIG. 4b the probe 1 is entirely enclosed in the capsule, and the bag opening 162 is closed from inside by the second lid 15. Lastly, the probe portion 10 is separated from the entrance lock (FIG. 4c), the hinges 121, 141 both being torn into two portions 121', 121" or 141', 141" respectively. Perforations 122, 142 in the hinges 121, 141 (FIG. 2) may facilitate separation. FIG. 8 shows a variant form of hinge 121' with snap-fastening-type joints, comprising two parts 225 and 226. A spherical projection 227 is received by a corresponding recess 228. The joint parts 225, 226 are joined on the left in FIG. 8 and separated on the right. Such hinges have the advantage over film hinges of being easily separated.

The edge of the bag opening 165 may for example be coated with an adhesive for the first lid 14, to provide releasable sealing of the bag 16. If a synthetic thermoplastic material is used for the bag and/or lid, sealing may also be effected by applying heat. The frame 140 may also be coated with adhesive on the interior at the contact points for the second lid 15. In addition, to ensure that the probe 1 is securely enclosed in the capsule, the contact surfaces between the shell portions 12 and 13, which come to bear on one another when the capsule is closed, may be at least partly coated with an adhesive. Instead of the adhesive, a snap fastening or pin closure may fulfil the same purpose.

For puncturing, the probe portion 10 is laid with the capsule wall 125 on the body. This capsule wall is made from a material which can be punctured by the puncturing needle, for example an elastomeric plastic material or gelatine.

Instead of the somewhat complicated ultrasound probe 1 it is possible to use a simple cylindrical probe 2 (FIG. 5). In this case, however, the probe portion 20 (FIG. 7) must be somewhat more complicated. The apparatus for preparing the puncturing device and the encapsulation of the ultrasound probe may be taken over substantially unchanged from the first embodiment. The capsule comprises the two shell portions 22, 23, which are connected at the cut surfaces 221', 241' by hinges 221, 241 to the other components of the entrance lock (FIG. 6). These components are again a first lid 24, a frame 240, a second lid 25 and a shield 244. The frame 240, as in the first embodiment, reinforces the opening of a bag (not shown). The shell portion 22 of the capsule is rigidly connected to the holder 21 and contains the electrical contacts 22c, 22d, by way of which the probe 2—by way of the connecting lead 211—can be connected to a stationary device portion (not shown). The corresponding contacts 2c, 2d on the probe 2 are for example annular, so that there is no need to ensure that the probe takes up a particular position when introduced into the entrance lock.

The ultrasound probe 2 is directed with its radiating end face 2h in the probe portion 20 facing the coupling member 30. This coupling member 30 contains the ultrasound reflector 31, formed for example by an oblique-cut metal cylinder with a longitudinal bore acting as a needle guide 32. The ultrasound beam transmitted is deflected on the reflector surface 31a onto the exit surface 225, the direction of the beam being coaxial with the direction of the needle guide 32. The space 35 between the reflector 31 and the exit surface 225 is filled, for example, with gelatine, which conducts ultrasound well.

The introduction of the ultrasound probe 2 into the capsule of the probe portion 20 is performed in substantially the same manner as in the first embodiment.

A variant embodiment of the apparatus as shown in FIG. 3 is illustrated in FIG. 9. The needle guide 123 (instead of 132) is mounted in the capsule portion 12 which is connected to the holder 11. The positions of the frame 140 and of the inner lid 15 are reversed as compared with the first embodiment. When the probe 1 or 1' is introduced, therefore, it enters the capsule portion 12. During the closing movement there is now no risk of the probe 1 or 1' being tipped out of the pivoted capsule portion 13. There is no need for a cover corresponding to the shield 144 (FIG. 2) and none is provided. The second embodiment (FIGS. 6, 7) can be modified in the same way, viz. by exchanging the positions of the lid 25 or frame 240, in which case again there is no shield 244.

FIGS. 10a to 10c illustrate a puncturing device in accordance with the invention, having a cylindrical probe 1" with an axial, laterally closed duct 1k. The capsule for the probe 1" is here formed by a cylindrical, socket-like portion 12' and a flat lid 13'. The capsule portion 12', shown in longitudinal section in FIG. 10c, contains the needle guide 123' onto which the duct 1k of the probe 1" fits. The upper end of the needle guide 123' bears a cap 124' which, during introduction of the probe 1", prevents contamination of the needle guide at its upper entry point. After insertion of the probe the cap 124' is removed. The capsule lid 13' has a recess 131', which is provided for the upper end of the needle guide 123'. This recess 131' is for example a blind bore closed by a perforable wall; alternatively, however, it may be formed by a hole fitting the needle guide 123'. The capsule lid 13' may be mounted so as to lie on the holder 11 as shown in FIG. 10b; alternatively, however, it may be mounted laterally—that is, turned through 90° relative to the axis of the needle guide 123'—or again on the opposite side or turned through 180°. The introduction apparatus comprising the two lids 14, 15 and frame 140' is substantially the same as in the embodiments described above; only the frame 140' has instead of a rectangular opening a circular one.

What is claimed is:

1. Apparatus for preparing a sterile puncturing device for blood vessels in which a non-sterile ultrasound probe can be used, comprising a fluid-tight bag forming a wall, a holder in the bag including a capsule for the ultrasound probe, and an entrance lock in the bag wall for introducing the ultrasound probe into the capsule, the entrance lock comprising a bag opening and a frame attached to the bag wall, a releasable first lid exteriorly connected with the frame for closing the bag opening, and a second lid interiorly connected with the frame for closing the bag opening following the introduction of the ultrasound probe.

2. Apparatus as claimed in claim 1, wherein an outer edge of at least one of the bag adjacent the opening and the frame is coated on its interior with an adhesive for at least one of the lids.

3. Apparatus as claimed in claim 1, including snap-fastening elements on an interior of the frame and on the second lid.

4. Apparatus as claimed in claim 1, the capsule for the ultrasound probe comprising at least two openable shell portions connected to the entrance lock of the bag prior to a receipt of the ultrasound probe therein.

5. Apparatus for use with a sterile blood vessel puncturing device and a non-sterile ultrasound probe, comprising a fluid-tight bag forming a wall, a holder in the bag and including a capsule for receiving the ultrasound probe, an entrance lock in the bag wall for introducing the ultrasound probe into the capsule, the capsule for the ultrasound probe comprising at least two openable shell portions connected to the entrance lock of the bag prior to the receipt of the ultrasound probe therein.

6. Apparatus as claimed in claim 5 including an entrance lock comprising a bag opening and a frame attached to the bag wall, a releasable first lid exteriorly connected with the frame for closing the bag opening, and a second lid interiorly connected with the frame for closing the bag opening following the introduction of the ultrasound probe.

7. Apparatus as claimed in claim 5 wherein a first of the two shell portions is connected to the frame and a second of the two shell portions is connected to the second lid of the bag opening by respective hinges.

8. Apparatus as claimed in claim 6, wherein at least one of the hinges is a film hinge.

9. Apparatus as claimed in claim 7, wherein the film hinge includes perforations for separation of the puncturing device from the entrance lock of the bag.

10. Apparatus as claimed in claim 6, wherein at least one of the hinges is formed by at least two snap-fastening joints.

11. Apparatus as claimed in claim 5 wherein the shell portions include contact surfaces which come to bear on one another when the capsule is closed, the contact surfaces including one of an at least partial coat of an adhesive and snap-fastening elements.

12. Apparatus as claimed in claim 5 wherein the capsule includes a coupling member for an ultrasound beam generated in the probe, the coupling member including a reflector for deflecting the ultrasound and a guide for a puncturing needle.

13. Apparatus as claimed in claim 5 including an ultrasound probe comprising first and second halves connected by a hinge and a recess is for a guide duct for a puncturing needle inside the capsule and extending along a longitudinal axis of the closed ultrasound probe.

14. Apparatus as claimed in claim 5 wherein the ultrasound probe has a groove for receiving a needle guide.

15. Apparatus as claimed in claim 5 wherein the ultrasound probe includes an axial, laterally closed duct, and wherein the capsule for the probe comprises a socket member having a needle guide and a lid.

* * * * *